US005951295A

United States Patent [19]
Lyles et al.

[11] Patent Number: 5,951,295
[45] Date of Patent: *Sep. 14, 1999

[54] CERAMIC FUSED FIBER ENHANCED DENTAL MATERIALS

[75] Inventors: Mark B. Lyles; Ronald G. Ritsco, both of San Antonio, Tex.

[73] Assignee: Materials Evolution and Development USA, Inc., San Antonio, Tex.

[*] Notice: This patent is subject to a terminal disclaimer.

[21] Appl. No.: 08/875,971

[22] PCT Filed: Feb. 8, 1996

[86] PCT No.: PCT/US96/01800

§ 371 Date: Aug. 8, 1997

§ 102(e) Date: Aug. 8, 1997

[87] PCT Pub. No.: WO96/24631

PCT Pub. Date: Aug. 15, 1996

[51] Int. Cl.$^6$ ................................ C08K 3/38; C08K 3/08; A61F 2/00

[52] U.S. Cl. ........................ 433/228.1; 524/404; 524/441; 524/492; 523/115; 523/116

[58] Field of Search ................................ 433/226, 228.1; 524/404, 441, 492; 523/115, 116

[56] References Cited

U.S. PATENT DOCUMENTS

| | | | |
|---|---|---|---|
| 3,721,644 | 3/1973 | Stoffey et al. . | |
| 4,239,113 | 12/1980 | Gross et al. | 260/568 |
| 4,381,918 | 5/1983 | Ehrnford | 433/199 |
| 4,392,828 | 7/1983 | Ehrnford | 433/217 |
| 4,650,847 | 3/1987 | Omura et al. | 526/376 |
| 4,707,504 | 11/1987 | Walkowiak et al. | 523/109 |
| 5,273,559 | 12/1993 | Hammar et al. | 51/298 |
| 5,621,035 | 4/1997 | Lyles et al. | 524/404 |

OTHER PUBLICATIONS

Gee, et al, Jan. 1993, True linear polymerization shrikage of unfilled resins and composites determined with a linometer; Dent Matar 9:11–14, pp. 11–14.
Feilzer, et al, Jan. 1993, Setting stresses in composites for two different curing modes; Dent Mater 9:2–5, pp. 2–5.
Hosoda, et al, Dec. 1990, SEM and elemental analysis of composite resins; The Journal of Prosthetic Dentistry, vol. 64, Num. 6, pp. 669–676.
Marshall, et al, Oct. 1988, Restorative Dental Materials: Scanning electron Microscopy and Xray Microanalysis; Scanning Microscopy, vol. 2, No. 4, pp. 2007–2028.
Johnson, et al, Aug. 1971, Effects of various finishing devices on resin surfaces;JADA, vol. 83, Aug. 1971, pp. 321–331.
Jaarda, et al, Apr. 1993, Measurement of composite resin filler particles by using scanning electron microscopy and digital imaging; The Journal of Prosthetic Dentistry, vol. 69, No.4, pp. 416–424.
Bowen & Antonucci, Jan. 1976, Dimethacrylate Monomers of Aromatic Diethers; Journal of Dental Resins May–Jun. pp. 599–604.

Kilfoil, et al, Jul. 1983, The tensile strength of a composite resin reinforced with carbon fibers; The Journal of Prosthetic Dentistry vol. 50, No. 1, pp. 40–43.
Hadavi, et al, Resin/Amalgam Bond Strength; Assessing Microleakage (Operative Dentistry).
Neo, et al, Dec. 1986, Effects of polymerization techniques of uniformity of cure of large–diameter, composite restorations; JADA, vol. 113, pp. 905–909.
Bowen, Feb. 1967, Adhesive bonding of various materials to hard tooth tissues; JADA vol. 74, pp. 439–445.
Asmussen, Jan. 1975, NMR–analysis of monomers in restorative resins; Acta Odont. Scand. 33, 129–134.
Brauer, et al, 1979, Effect of Diluent on the Properties of Bis–GMA Based Composites; IADR Abstracts 1979, p. 243.
Antonucci Bowen, Jul. 1975, Dimethacrylates Derived From Hydroxybenzoic Acids; J Dent Res Jan.–Feb. pp. 8–15.
Caldwell, et al, Oct. 1957, Michrohardness studies of intact surface enamel; J. Dent. Res., pp. 732–738.
Ryge, et al, Dec. 1961, Micro–identation Hardness; J. D. Res., vol. 40, No. 6, pp. 1116–1126.
Atmadja, 1990, Some factors influencing the depth of cure of visible light–activated composite resins; Australian Dental Journal 1990;35(3): 213–18.
Braem, et al, Nov. 1985, The impact of Composite Structure on Its Elastic Response; J. Dent. Res., vol. 65, No. 5, pp. 648–653.
Nakayama, et al, Nov. 1973, Elastic properties of dental resin restorative materials;Journal of Dent Res, Sep.–Oct., vol. 53, No. 5.
Fan, et al, Nov. 1979, In vitro wear of microfilled and visible light–cured composites; J. Dent Res, Nov., vol. 58, No. 11.
Mitchem, Gronas, Dec. 1985, The continued in vivo evaluation of the wear of restorative resins; JADA Research Reports, vol. 111, Dec. pp. 961–964.
Craig, Apr. 1981, Chemistry, Composition, and Properties of Composite Resins; Dental Clinics of North America—vol. 25, No. 2.
Leinfelder, Apr. 1981, Composite resins in posterior teeth; Dental Clinics of North America—vol. 25, No.2 pp. 357–364.
Lambrechts, et al, Sep. 1991, The surface roughness of enamel–to–enamel contact areas scared with the intrinsic roughness of dental composites; J Dent Res, SeptVol. 70, No. 9, pp. 1299–1305.

(List continued on next page.)

*Primary Examiner*—Ralph A. Lewis
*Attorney, Agent, or Firm*—Frohwitter

[57] ABSTRACT

The preferred embodiment of the present invention provides novel and unique filler compositions and ceramic enhanced dental materials. The preferred embodiment of the composition and the ceramic dental restorative materials made therefrom comprise a rigid three-dimensional network of fibers fused together at their points of contact wherein said network is greater than 60% by volume void space, has mean pore diameters greater than 10 microns, or both.

34 Claims, 7 Drawing Sheets

OTHER PUBLICATIONS

Fan Powers, Dec. 1980, In vitro wear of aged composite restorative materials; J Dent Res, vol. 59, No. 12, pp. 2066–2070.

Hosoda, Dec. 1990, EM and elemental analysis of composite resins; Journal of Prosthetic Dentistry, vol. 64, No. 6, pp. 669–676.

Bowen & Marjenhoff, Sep. 1992, Dental Composites/Glass Ionomers: The Material; Adv Dent Res 6: 44–49.

Lambrech Braem, Sep. 1992, A classification of dental composites according to their morphological and mechanical characteristics; Dent Mater 8:310–319.

Jun. 1977, New American Dental Association Specification No. 27 for Direct Filling Resins; Reports of Councels and Bureaus / JADA, vol. 94, pp. 1191–1194.

Leinfelde, Apr. 1985, Composite Resins; Dental Clinics of North America—vol. 29, No. 2, pp. 359–371.

Lutz Phillips, Oct. 1983, A classification and evaluation of composite resin systems; Fixed Prosthodontics / Operative Dentistry, vol. 50, No. 4, pp. 480–488.

Lambrech Vanherle, 1983, Structural evidences of the microfilled composites; vol. 17, 249–260.

Craig, May 1979, Selected Properties of Dental Composites; J Dent Res, vol. 58, No. 5, pp. 1544–1550.

Braem, Finger, Sep. 1989, Mechanical properties and filler fraction of dental composites; Dent Mater 5:346–349.

Ameye, Lambrech, 1981, Conventional and microfilled composite resins. Part I: Color stability and marginal adaptation; Journal of Prosthetid Dentistry, vol. 46, No. 6, pp. 623–630.

Robinson McCabe, Nov. 1993, Impact strength of acrylic resin senture base materials with surface defects; Dental Materials 9:355–360.

Bowen, Jan. 1963, Properties of a silica–reinforced polymer for dental restorations; Journal of the American Dental Association, vol. 66, pp. 57–64.

Bowen, Oct. 1964, Effect of particle shape ansd size distribution in a reinforced polymer; Journal of the American Dental Association, vol. 69, pp. 481–495.

Mabie Menis, 1978, Microporous Glassy Fillers for Dental Composites; Journal of Biomedical Materials Research, vol. 12, 435–472.

Soderhol, Nov. 1981, Degradation of Glass Filler in Experimental Composites; J Dent Res 60(11):1867–1875.

Ruyter, Aug. 1988, Composites–Characterization of composite filling materials: Reactor Response; Adv Dent Res 2(1):122–129.

Leinfelde, Aug. 1988, Current Developments in Posterior Composite Resins; Adv Dent Res 2(1):115–121.

Raptis, Fan, Pow, Oct. 1979, Properties of microfilled and visible light–cured composite resins; JADA, vol. 99, pp. 631–633.

Lacy, Mar. 1987, A critical look at posterior composite restorations; JADA, vol. 114, pp. 357–362.

Hinoura Moore, Feb. 1987, Tensile bond strength between glass ionomer cements and composite resins; JADA, vol. 114, pp. 167–172.

Dennison Craig, Jul. 1972, Physical properties and finished surface texture of composite restorative resins; JADA, vol. 85, pp. 101–108.

Asmussen, 1985, Clinical Relevance of Physical, Chemical, and Bonding Properties of Composite Resins; Operative Dentistry, vol. 10, pp. 61–73.

Davidson Gee, Feb. 1984, Relaxation of Polymerization Contraction Stresses by Flow in Dental Composites; J Dent Res 63(2):146–148.

Stanford Fan, Nov. 1987, Radiopacity of light–cured posterior composite resins; JADA, vol. 115, pp. 722–724.

Fan, Edahl, Jan. 1985, Alternative Interpretations of Water Sorption Values of Composite Resins; J Dent Res 64(1):78–80.

Dennison Powers, Apr. 1978, Color of Dental Restorative Resins; J Dent Res 57(4):557–562.

Ferracane Moser, Sep. 1981, Rheology of Composite Restoratives; J Dent Res 60(9):1678–1685.

Hirasawa Hirano, Jan. 1983, Initial Dimensional Change of Composite in Dry and West Conditions; J Dent Res 62(1):28–31.

Oysaed Ruyter, Nov. 1986, Water Sorption and Filler Characteristics of Composites for Use in Posterior Teeth; J Dent Res 65(11):1315–1318.

Powers Hostetler, Feb. 1979, Thermal expansion of composite resins and Sealants; J Dent Res 58(2):584–587.

Braden, Aug. 1988, Some aspects of the chemistry and physics of dental resins; Adv Dent Res 2(1):93–97.

Vallittu, A review of reinforcing the polymethyl methacrylate with metal strengtheners; pp. 1–40 plus figures.

Goldberg Burstone, May 1992, The use of continuous fiber reinforcement in dentistry; Dent Mater 8:197–202.

Ritsco, Sprg 1994, Applications of Fibers in Prosthetic Dentistry; Dental Material and Research, pp. 1–13.

Ehrnford, Oct. 1981, Composite resins with a condensable inorganic phase; J Dent Res 60(10):1759–1766.

Ehrnford, 1976, A method for reinforcing dental composite restorative materials; Odont. Revy 27:51–54.

Cross Douglas, Jul. 1983, The relationship between filler loading and particle size distribution in composite resin technology; J Dent Res 62(7):850–852.

Ehrnford, 1984, Surface characteristics of composite resins comprising a porous reinforcing filler; Acta Odontol Scand 42 pp. 59–64.

Latour Black, 1992, Development of FRP composite structural biomaterials: Ultimate strength of the fiber/matrix interfacial bond in in vivo simulated environments; Journal of Biomedical Materials Research, vol. 26, 593–606.

Kilfoil Hesby, Jul. 1983, The tensile strength of a composite resin reinforced with carbon fibers; Journal of Prosthetic Dentistry, vol. 50, No. 1, pp. 40–43.

Goldberg, 1994, Screening of matrices and fibers for reinforced thermoplastics intended for dental applications; Journal of Biomedical Materials Research, vol. 28, 167–173.

Bowman, 1984, The elimination of breadages in upper dentures by reinforcement with carbon fibre; British Dental Journal vol. 156 pp. 87–89.

Smith, 1962, Recent developments and prospects in dental polymers; British Dental Journal, vol. 12, No. 6, pp. 1066–1078.

Grant Greenert, Feb. 1967, Wisker reinforcement of polymethyl methacrylate denture base resins; Australian Dental Journal pp. 29–33.

DeBoer Vermilye, 1984, The effect of carbon fiber orientation on the fatigue resistance and bending properties of two denture resins; Journal of Prosthetic Dentistry, pp. 119–121.

Schreiber, Jul. 1974, The clinical application of carbon fibre/polymer denture bases; Brit Dent J 1974, 137, 21.

Vallittu Lassila, 1992, Reinforcement of acrylic resin denture base material with metal or fiber strengtheners; Journal of Oral Rehabilitation, vol. 19, pp. 225–230.

Skirvin Vermilye, Dec. 1982, Polymethylmethacrylate reinforcement: Effect on fatigue failure; Military Medicine, vol. 147, pp. 1037–1040.

Grave Chandler, Jun. 1985, Denture base acrylic reinforced with high modulus fibre; Dent Mater 1985:1: 185–187.

Ruffino, 1985, Effect of steel strengtheners on fracture resistance of the acrylic resin complete denture base; Journal of Prosthetic Dentistry, vol. 54, No. 1, pp. 75–77.

Schreiber, Jan., 1971, Polymethylmethacrylate Reinforced with Carbon Fibres; Brit Dent J 1971, 130, 29–30.

Gutteridg, 1992, Reinforcement of poly(methylmethacrylate) with ultra–high–modulus polyethylene fibre; J. Dent. 1992; 20: 50–54.

Braden, 1988, Denture base poly(methyl methacrylate) reinforced woth ultra–high modulus polyethylene fibres; Br. Dent. J. 1988; 164:109–112.

Andreopo Papaspyri, Jan. 1991, Surface treated polyethylene fibres as reinforcement for acrylic resins; Biomaterials, vol. 12, pp 83–87.

Gutteridg, 1988, The effect of including ultra–high–modulus polyethylene fibre on the impact strength of acrylic resin; British Dental Journal 1988; 164: 177, pp. 177–180.

Edstrand Ruyter, 1986, Implant–fixed, dental bridges from carbon/graphite fibre reinforced poly (methyl methacrylate); Biomaterials 1986, vol. 7 Jan., pp. 73–75.

O'Brien, 1989, Dental Materials: Properties and Selection; Quintessence Publishing Co., Inc. 1989, pp. 157–170.

Ruyter Ekstrand, 1985, Development of carbon/graphite fiber reinforced poly(methyl methacrylate) suitable for implant–fixed dental bridges; Dent Mater 1986: 2; 6–9.

Malquati Berruet, 1990, Prosthetic use of carbon fiber–reinforced epoxy resin for esthetic crowns and fixed partial denures; J Prosthet Dent 1990; 63: 251–7.

Markus, 1994, An indirect/direct combined approach for a reinforced fixed bridge; Journal of the New Jersey Dental Association/Winter 1994, pp. 23–26.

Nov. 1993, Product Spotlight—GlasSpan Flexible Ceramic Bonded Reinforcement Material—The Indirect GlasSpan Bridge; Trends & Techniques; Nov. 1993, pp. 24–25.

Altieri Burstone, Jan. 1994, Longitudinal clinical evaluation of fiber–reinforced composite fixed partial dentures: A pilot study; Prosthet Dent 1994; 71:16–22.

Burgess, Mar. 1993, Flexural Strength of Five Provisional Materials; IADR General Session and Exhibition, Seattle Washington.

Andreopo Petsalas, 1992, Reinforcement of acrylic polymers with rediopaque cellulose fibres; Journal of material Science; 27: 734–36.

Willems Lambrech, 1993, Composite resins in the 21st century; Quintessence International vol. 24, Num. 9, pp. 641–657.

Albers, 1991, ADEPT Report; vol.2, No. 4, pp. 53–64.

Farah, 1991, Anterior and Posterior Composites; The Dental Advisor; 1–8.

Tantalum Oxides and Fused Fibrous Silica as an alternative to contemporary Posterior composite fillers; Research Methodology II, pp. 1–5.

\* PRIMM™ with colloidal silica
\*\* PRIMM™ with colloidal silica plus silanated resin \* PRIMM™ with colloidal silica
\*\* PRIMM™ with colloidal silica plus silanated resin

CERAMIC FUSED FIBER ENHANCED DENTAL MATERIALS

FIELD OF THE INVENTION

This invention relates to dental restorative materials. In another respect, the invention relates to ceramics and ceramic composite restorative materials. Yet in another aspect, the invention relates to novel restorative compositions, including but not limited to, silver-based mercury amalgams, castable ceramic/porcelain compositions, ceramic/metal hybrids, and plastic-based denture or denture-like materials for the direct or indirect restoration or replacement of teeth or other oral anatomical structures. In a further aspect, the invention relates to novel restorative compositions for the direct filling of posterior teeth.

BACKGROUND OF THE INVENTION

Dental restorative materials include materials used to repair damaged teeth and/or replace missing teeth and/or other related oral structures. In some instances, dental restorative materials include materials used to reconstruct the maxillofacial complex. In general, dental restorative compositions include: (1) dental metal based amalgams, (2) enamel and dentin bonding agents, (3) dental hybrid composites, (4) dental cements and bases, (5) casting alloys for crowns and bridges and other prosthetic structures, (6) ceramic/metal materials, (7) denture and prosthetic devices, (8) filled polymeric resins, (9) ceramic-based restorative materials, (10) impression materials, (11) sealants, and (12) temporary restorations and crowns, etc. The present invention relates to dental hybrid composite resins, denture and prosthetic materials, dental metallic based amalgams, temporary restorations and crowns, sealants, bases, cements, bonding agents, and ceramic porcelain restorative materials.

A variety of compositions have been proposed and used for the direct filling of teeth. Of these compositions, some may be generally classified as dental composites and more specifically as resin composites. These resin composites are comprised of inorganic particulates, i.e., filler, bound together with a polymeric matrix, i.e., a binder. The particulate filler reinforces the polymeric matrix and offsets its deficiencies. The binder, and/or polymeric matrix, may be comprised of an acrylic or epoxy resin or other types of carbon-based polymers. See, for example, U.S. Pat. Nos. 3,066,112 and 3,179,623 which are hereby incorporated by reference. Fillers for such composite compositions, both posterior and/or anterior dental use, include finely divided solids like fumed silica, glass, zirconium, aluminum oxide, crystalline quartz, glass beads, or a mixture of glass beads and quartz or mixtures of the above materials. A material acceptable, however, for posterior use must be able to achieve a high filler loading capacity in the resin system. Moreover, filler strength, content, shape and size directly determines the physical and mechanical properties of the restoration material.

To date, there has been no composite material developed that completely meets the expected parameters needed for the intended use as a posterior dental restorative material to replace mercury-based dental amalgams. Dental materials presently available lack several physical or mechanical properties necessary for an ideal posterior dental restoration. As noted, it is imperative to achieve a high filler loading capacity in the resin system and presently all attempts to achieve such have failed. For example, highly loaded materials such as Microfine Composite™, using colloidal silica of a 40 nm size result in dramatically increased viscosity which jeopardizes handling characteristics. (See, Lambrechts, P; Vanherle, G. (1983); *Structural Evidence of Microfilled Composites. J. Biomed Mater Res* 17:249–60; Willems, G; Lambrechts, P.; Braen, M; Celis, J. P.; Vanherle, G. (1993): *A Classification of Dental Composites according to their Morphology and Mechanical Characteristics. Dent Mater* 8:310–19). The colloidal silica forms an extended network structure that produces an increase in viscosity thereby limiting the amount of filler that can be incorporated to around 50% by volume. This 50% volume of filler loading has only been obtained by first filling to a higher degree, that is, greater than 50% during manufacturing, and then curing under high temperature and grinding to make colloidal oxide field resin particles (organic fillers). However, a major problem still remains. The interface between these particles and the matrix, i.e., binder, is weak and causes brittle failure and wear. The filler composition of the present invention has the characteristics needed for posterior composite materials when combined with a resin matrix to address and solve these major hurdles.

The properties needed for an advantageous dental restorative material include, inter alia, the following: (1) low to high density, (2) high tensile/compression strength, (3) low thermal conductivity, (4) purity, (5) long life in cyclic applications, (6) high flexural strength, (7) rigidity, (8) inertness, (9) dimensional stability, (10) thermal shock resistance, (11) high diffusivity, (12) biocompatibility and (13) porosity. The present invention provides heretofore unknown fused-fibrous dental restorative materials with the above properties.

SUMMARY OF THE INVENTION

An object of the present invention is to provide fused-fibrous/highly porous filler materials useful in dental fillings and materials that are particularly useful in dental restorative compositions, prosthedontic applications, and ceramic restorative materials, which have improved handling characteristics, improved strength, improved wear resistance, and decreased shrinkage from polymerization as compared to presently available dental restorative compositions, dental prosthetic devices, and ceramic restorative materials. The composition of the present invention also contains less than 1% cristobalite contamination. It has been discovered that significantly improved particulates that are useful as fillers in dental restorative and prosthetic compositions are obtained from fused-fibrous compounds manufactured from: (1) from about 1% to about 50% by weight alumina; (2) from about 50% to about 98% by weight silica; and (3) from about 1% to about 5% by weight boron. In addition, the composition may further comprise silicon carbide up to about 3% by weight. Also, the present invention is directed to a filler/reinforcer which is comprised of over 99% silica. The invention includes methods for the direct filling of teeth utilizing the filler/reinforcer of the present invention with an initially liquid settable filling material comprising, in addition to filler, a binder wherein the material is allowed to harden after insertion in a tooth. In addition, the present invention provides reinforced dental restorative materials comprising a rigid three-dimensional network of inorganic or organic fibers fused together at their points of contact wherein said network has mean pore diameters of greater than 10 microns, or is 60% or greater by volume void space, or both.

DESCRIPTION OF THE PREFERRED EMBODIMENTS

Figure 1:
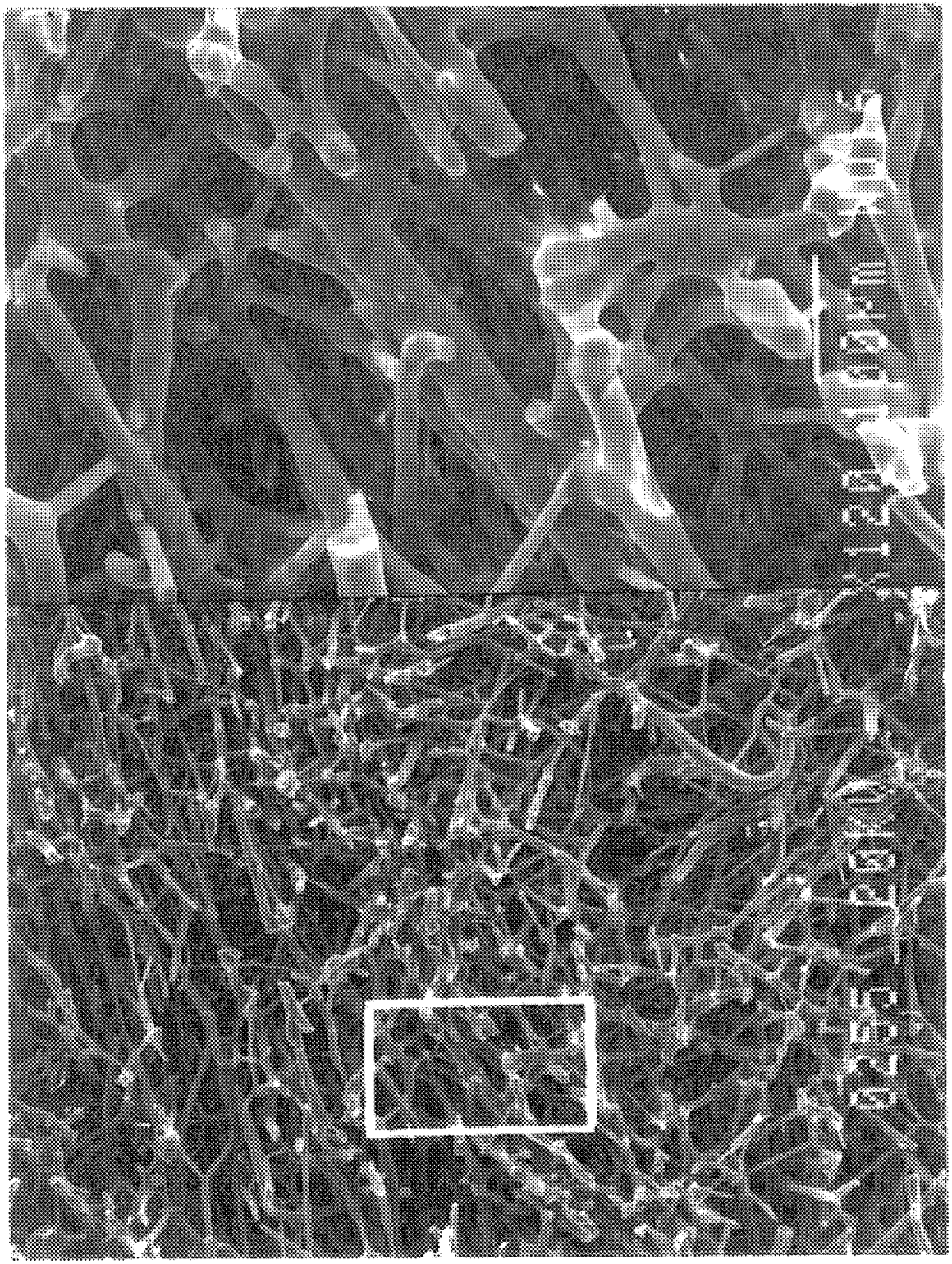
FIG. 1 is a scanning electron micrograph of the material of the present invention at 6 lb/ft$^3$.
Figure 2:
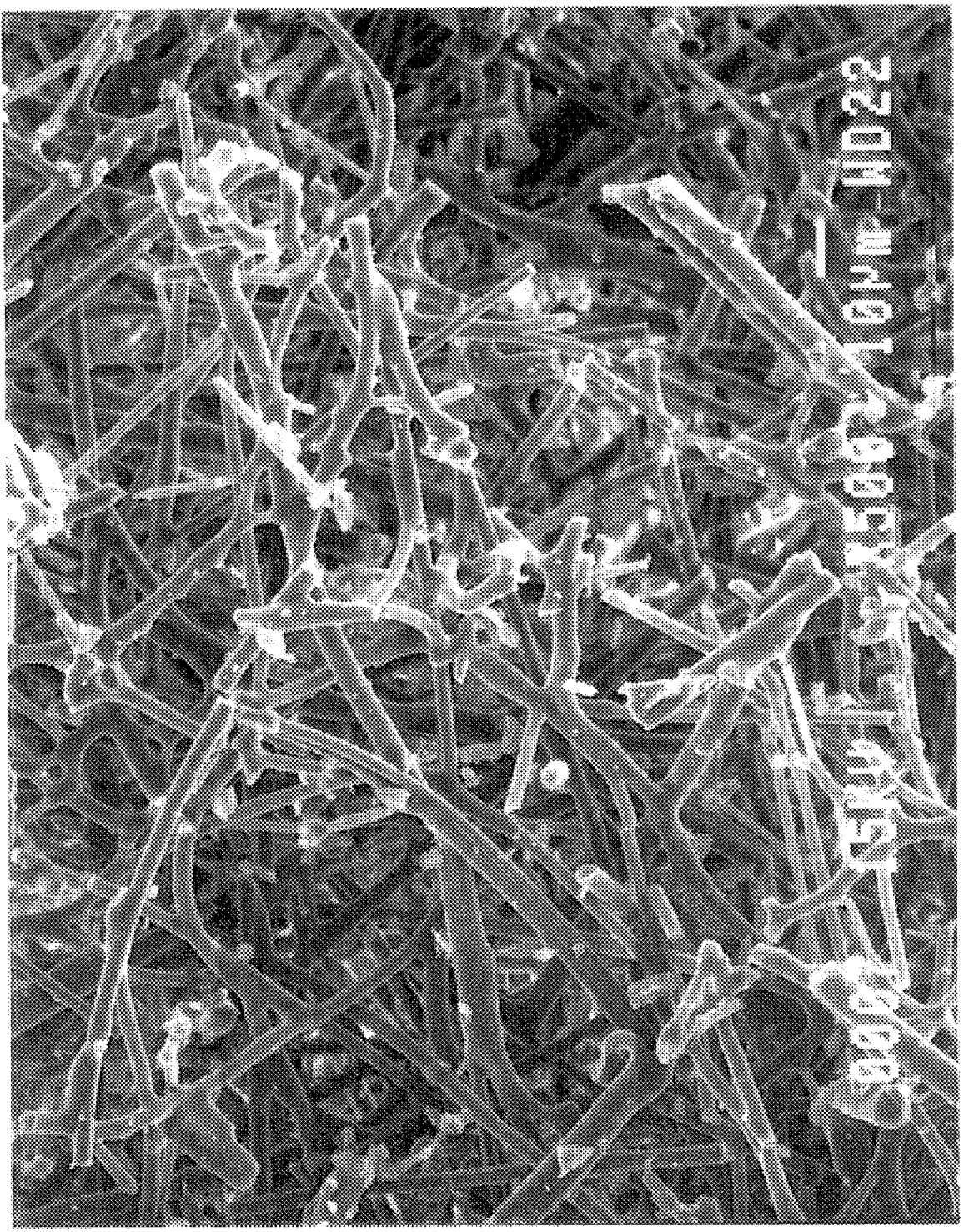
FIG. 2 is a scanning electron micrograph of the filler/reinforcer material of the present invention at 16 lb/ft$^3$.

Generally, the filler components of the present invention has been described above in the Summary Of The Invention. However, several fused-fibrous filler compositions falling within the description set forth above are particularly preferred. Generally, the compositions of the present invention are manufactured utilizing alumina fibers, silica fibers, and from about 1% to about 5% boron, preferably boron nitride.

One preferred embodiment is comprised of a binder and a filler wherein said filler is comprised of about 1% to about 50% by weight alumina, from about 50% by weight to about 98% by weight silica, and boron. Another preferred embodiment is manufactured utilizing: (1) from about 15% to about 30% by weight alumina fiber; (2) from about 65% to about 85% by weight silica fiber; (3) from about 1% to about 3% by weight silicon carbide; and (4) from about 1% to about 5% by weight boron nitride.

Another more preferred fused-fibrous composition for the filler is manufactured from: (1) about 21% by weight alumina fiber; (2) about 74% by weight silica fiber; (3) about 2% by weight silicon carbide; and (4) about 2.85% by weight boron nitride. Preferably, the material of the present invention is manufactured utilizing alumina and silica fibers in a ratio of 22:78 by weight. For strength, a preferred ratio of alumina to silica is 30:70 by weight.

Moreover, a preferred embodiment of the composition of the filler, or reinforcement, of the present invention comprises: a rigid three-dimensional network of inorganic or organic fibers fused together at their points of contact wherein said network has a mean pore diameters of greater than about 10 microns, or has greater than about 60% by volume void space, or both.

The ceramic/resin hybrid restorative materials of the present invention have the advantageous properties outlined above needed for dental restorative composites and prosthetic materials. The filler material alone, has exceptional physical, chemical, and mechanical properties which are imparted to varying degrees depending upon the application to dental restoratives manufactured utilizing the material, these properties include, inter alia: (1) low to high density—4 lb./ft.$^3$ to 62 lb./ft.$^3$; (2) low thermal conductivity—e.g., for 12 lb./ft.$^3$ density at 500° F. conductivity=0.61 Btu—in./ft.$^2$; (3) purity—predominately comprised of 99.7% pure silica fibers and 95.2% pure alumina fibers; (4) long life in cyclic applications—e.g., 12 lb./ft.$^3$ density, does not degrade with cyclic exposure to 2600° F. and can even withstand limited exposure to 2900° F.; (5) rigidity—maintains shape and supports mechanical loads while providing thermal insulation (i.e., has a high compressive strength and tensile strength (MN/m2) (6) high flexural strength—modulus of rupture for 4 lb./ft.$^3$ to 62 lb./ft.$^3$ densities ranges from 100–6200 lb./in.$^2$; (7) inert—does not burn, softens at temperatures above 2700° F. and melts at about 3100° F.; (8) dimensional stability—has a low coefficient of thermal expansion and 0.4% linear shrinkage; (9) thermal shock resistance—can be heated to 2600° F. and immediately immersed in cold water without damage; (10) high diffusivity—12 lb./ft.$^3$ to 62 lb./ft.$^3$ ranges from 97% to 56%; (11) porosity—highly porous (over 60% by volume void space, preferably between about 60% and about 98% by volume void space, most preferably over 80% by volume void space) and offers minimal resistance to the passage of gases or liquids (mean pore diameters greater than 10 microns, generally between 10 and 25 microns, most preferably from about 20 to about 22 microns); (12) able to coat or bond to other materials (i.e., materials, plastics, metals, inorganics) with relative ease to enhance characteristics. In addition, the 16 lb/ft$^3$ density filler material of the present invention has (1) a flexural modulus of strength—2.5×10$^{10}$ Pa, (2) a Rockwell Hardness—50, (3) Surface Roughness of 0.6 Ra, and (4) linear shrinkage of 0.4% after repeated cycles at temperatures above 2700° F. As a result, e.g., the composite resins made with the filler of the present invention have heretofore unknown linear shrinkages of less than about 0.09%.

Generally, the process for the manufacture of fused-fibrous silica/alumina and/or other ceramic fiber of low density, like 16 lb. per ft.$^3$, is comprised of the following steps:

(1) preparation of a slurry mixture comprised of pre-measured amounts of purified fibers/materials and deionized water;

(2) removal of shot from slurry mixture;

(3) removal of water after thorough mixing to form a soft billet;

(4) addition of a ceramic binder after the formation of the billet;

(5) placement of the billet in a drying microwave oven for moisture removal; and (6) sintering the dry billet in a large furnace at about 1600° F. or above.

The high purity silica fibers above are first washed and dispersed in hydrochloric acid and/or deionized water or other solvents. The ratio of washing solution to fiber is between 30 to 150 parts liquid (pH 3 to 4) to 1 part fiber. Washing for 2 to 4 hours generally removes the surface chemical contamination and non-fibrous material (shot) which contributes to silica fiber devitrification. After washing, the fibers are rinsed 3 times at approximately the same liquid to fiber ratio for 10 to 15 minutes with deionized water. The pH is then about 6. Excess water is drained off leaving a ratio of 5 to 10 parts water to 1 part fiber. During this wash and all following procedures, great care must be taken to avoid contaminating the silica fibers. The use of polyethylene or stainless steel utensils and deionized water aids in avoiding such contamination. The washing procedure has little effect on the bulk chemical composition of the fiber. Its major function is the conditioning and dispersing of the silica fibers.

The alumina fibers are prepared by dispersing them in deionized water. They can be dispersed by mixing 10 to 40 parts water with 1 part fiber in a V-blender for 2½ to 5 minutes. The time required is a function of the fiber length and diameter. In general, the larger the fiber, the more time required.

Generally, in order to manufacture ultra-low density fused-fibrous ceramic filler material, for example, densities below 12 lb./ft.$^3$, the process includes the additional steps of:

(1) the addition of expendable carbon fibers in the casting process and/or other temporary support material; and (2) firing the billet at about 1300° F. to remove the carbon fibers or other support material prior to the final firing at approximately 1600° F. or above.

When the dispersed silica fibers and dispersed alumina fibers are combined, the pH is probably acidic and should be adjusted to neutral with ammonium hydroxide. The slurry should contain about 12 to about 25 parts water to about 1 part fiber. The slurry is mixed to a uniform consistency in a V-blender in 5 to 20 minutes. The boron nitride can be added at this point (2.85% by weight of the fibers) and mixed to a uniform consistency in a V-blender for an additional 5 to 15 minutes creating a Master Slurry. The preferred mixing procedure uses 15 parts water to 1 part fiber and the slurry is produced in about 20 minutes of mixing. At lower density formulations, expendable carbon fibers are used to give "green" strength to the billet prior to the final sintering. The percent of carbon fiber used varies greatly depending on the diameter, length and source of the fiber and the ultimate density of the material being produced. The percent of carbon fiber per dry weight of material should range between 1 and 10%. The source of the carbon fiber can take many forms including nylon, cellulose, and purified graphite based carbon in fibrous form. Carbon fibers added in the casting process are eliminated by firing the billets at 1350° F. prior to the final firing at 2450° F.

The Master Slurry is poured into a mold for pressing into the desired shape. The water is withdrawn rapidly and the resulting felt is compressed at 10 to 20 psi. Rapid removal of the water is required to prevent the fibers from separating. If graded properties are desired in the resultant material, the slurry can be allowed to settle and the fibers to partially separate before the removal of the water.

The final density of the finished restorative material is determined in part by the amount of compression placed on the felt, varying the wet molded dimension in relation to the fiber content. The formulation of the present invention has been prepared in densities ranging from about 0.05 to 0.48 g/cc. It can, however, be prepared in lower and higher densities.

After molding, the restorative material is dried and fired by the following preferred procedure. The material is first dried in an oven for 18 hours; the temperature, initially 38° C., is raised at a rate of 11° C. per hour to 104° C., held there for 4 hours, raised again at a rate of 11° C. per hour to 150° C., and held there for 4 hours. The material is taken directly from the drying oven, placed in the firing furnace, and fired. A temperature rise rate of 220° C. per hour or less is required in order to avoid cracking and warping in the case of a 15 cm×15 cm×7.5 cm block of material. For larger blocks, slower heating rates may be required. The maximum firing temperature may vary from 1200° C. to 1600° C. depending upon the fiber ratio used, amount of boron nitride, and the final density of the material that is desired.

The temperature rise rate is chosen to permit relatively uniform temperatures to be achieved throughout the material during the process. A faster temperature rise rate causes non-uniform temperatures to be achieved throughout the material during the process. A faster temperature rise rate causes nonuniform strength and density and may cause cracking. Longer or higher temperature firing results in higher shrinkage and related greater resistance to subsequent shrinkage, as well as a shorter lifetime to devitrification under cyclic exposures to high temperatures. The maximum firing temperature is dependent upon the fiber ratio used and the density of the composite desired. The firing time and maximum temperature are selected to allow sufficient shrinkage to achieve stabilization and fiber fusion while not allowing any devitrification.

After firing, the material may be machined to obtain any desired final dimensions. Only about 0.5 cm of the material must be machined off.

The procedure used to prepare this restorative material, i.e., the polymeric rigid inorganic matrix material of the present invention, may be varied through a rather broad range with satisfactory results. In one variation, the silica fibers may be borated and prefired prior to use. This process is used to improve the morphological stability and physical properties of the resultant material.

The following examples are provided to illustrate the invention by describing various embodiments, including its best mode as presently conceived. All proportions used are expressed on a percent by weight basis unless otherwise noted.

EXAMPLE 1

An embodiment of the fused-fibrous matrix ceramic material of the present invention having a density of 0.32 g/cc, and opacified with silicon carbide was produced, with 825 grams of silica fibers, 175 grams alumina fiber (average diameter—11 microns, length—0.32 cm), 35 grams 1200 grit silicon carbide, 2.85 grams of boron nitride, 10 milliliters hydrochloric acid, 5 milliliters ammonium hydroxide and deionized water. The silica fibers were washed as in Example 2.

The alumina fibers were placed in a 7,570 ml capacity stainless steel double shell blender with 5,000 grams deionized water and mixed using an intensifier bar for 2½ minutes to disperse the fiber.

The washed silica fibers, dispersed alumina fibers, boron nitride, and silicon carbide were placed in a 28.31 liter stainless steel double shell V-blender. Deionized water was added to bring the total weight to 15,000 grams. The ammonium hydroxide (5 ml) was added to adjust the slurry to basic before mixing. The slurry was mixed, degassed, transferred to a mold and pressed into a billet as in Example 2.

EXAMPLE 2

The materials used were the following: 150 grams aluminasilicate fibers (AS-32, manufactured by 3-M Company containing 80% $Al_2O_3$ and 20% $SiO_2$), 1000 grams of silica fibers (Microquartz 108), 35 grams of 1200 grit silicon carbide, 30 grams of boron nitride, 10 ml of hydrochloric acid, 5 ml of ammonium hydroxide, and deionized water.

The silica fibers were placed in a polyethylene container in 32 liters of deionized water. Hydrochloric acid (10 ml) was added to bring the pH to 3. Pure nitrogen was bubbled through the mixture to agitate the fiber and assist washing. Agitation was continued for two hours. The acidic water was then drained off, fresh deionized water added and the mixture again agitated with pure nitrogen for 15 minutes. The rinsing process was repeated 2 more times which brought the pH to about 6.0.

The aluminasilicate fibers were placed in a 7,570 ml capacity stainless steel double shell blender with 5,000 grams of deionized water and mixed using the intensifier bar for 2½ minutes to disperse the fiber.

The washed silica fibers, dispersed aluminasilicate fibers, boron nitride, and silicon carbide were placed in a 28.31 liter stainless steel double shell V-blender. Deionized water was added to bring the total weight to 18,000 grams. Ammonium hydroxide (5 ml) was added to adjust the slurry to basic before mixing. The slurry was then mixed with the intensifier bar running for 20 minutes, removed from the V-blender and degassed, transferred into a mold, and pressed into a 21.6 cm×21.6 cm×10 cm billet. The top and bottom of the mold were perforated and covered with a 16 mesh aluminum screen to allow the excess water to flow out.

The billet was dried in an oven for 18 hours beginning at 38° C., increased at 11° C. per hour to 104° C., held for four hours at 104° C., increased at 11° C. per hour to 150° C. and held four hours at 150° C. After drying, the billet was transferred to the firing furnace. The furnace temperature was increased at a rate of 220° C. per hour to the firing temperature, 1315° C., where it was held for 1½ hours. After firing, the temperature was decreased at a rate of 220° C. per hour to 980° C. where the furnace was turned off, then allowed to cool to room temperature.

The usefulness of boron oxide in the two-fiber composites of this invention is demonstrated by the following preparations.

EXAMPLE 3

In one run, an experimental mixture was made containing 25% aluminasilicate fibers ("FIBERFRAX H," manufactured by the Carborundum Company, containing 62% $Al_2O_3$ and 38% $SiO_2$) and 75% pure silica fibers ("MICROQUARTZ 108"). The mixture was ground with mortar and pestle and then fired at 1400° C. for 5 hours. The resulting product underwent 48% devitrification. When the aluminasilicate fibers were prefired with boron oxide (85% and 15% respectively) at 1100° C. for 90 minutes and then mixed with the silica fibers and fired as above, the product exhibited no devitrification.

EXAMPLE 4

An acceptable 17 cm×17 cm×7.5 cm billet of material having a density of 0.11 g/cc was produced using 600 grams of silica fibers, 90 grams of aluminaborosilicate fibers (average diameter-11 microns, 0.64 cm long), 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 3000 grams of deionized water for 5 minutes. The washed silica fibers, dispersed aluminaborosilicate fibers, and ammonium hydroxide were mixed, with enough deionized water to bring the total weight to 9,000 grams, in a 28.31 liter V-blender for 10 minutes with the intensifier bar running. The slurry was removed from the V-blender, degassed, molded and the resulting billet fired as in Example 2. The billet was then transferred to the firing furnace. The furnace temperature was increased at a rate of 220° C. per hour to the firing temperature, 1260° C., where it was held for 5 hours. After firing, the temperature was decreased at a rate of 220° C. per hour to 980° C., at which point the furnace was turned off and allowed to cool at room temperature. The billet was machined to 17 cm×17 cm×7.5 cm in accordance with usual machining practices.

EXAMPLE 5

An acceptable 17 cm×17 cm×7.5 cm billet of material with yet greater stability toward devitrification than the material produced in example 1, having a density of 0.32 g/cc, and opacified with silicon carbide was produced using 825 grams of silica fibers, 175 grams aluminaborosilicate fibers (average diameter-11 microns, 0.64 cm long), 35 grams of 1200 grit silicon carbide, 10 ml of hydrochloric acid, 5 ml of ammonium hydroxide, 56.8 grams of boron oxide, and deionized water.

The silica fibers were washed in accordance with the procedure of Example 2. The boron oxide was dissolved in 4,000 grams of deionized water (concentration-1.42% boron oxide). The aluminaborosilicate fibers were placed in a stainless steel basket and dipped into the boron oxide solution (the aluminaborosilicate fibers absorbed 7 times their own weight of the boron oxide solution). The fibers with absorbed boron oxide were then dried at 104° C. for 4 hours and calcined at 1100° C. for 1 hour. The "borated" fibers were then placed in a 7,570 ml capacity stainless steel V-blender with 5,000 grams of deionized water and mixed using the intensifier bar for 2½ minutes to disperse the fiber. The washed silica fibers, dispersed "borated" aluminaborosilicate fibers, silicon carbide, and ammonium hydroxide were mixed with enough deionized water to bring the total weight to 15,000 grams, in a one cubic foot V-blender for 20 minutes with the intensifier bar running. The slurry was removed from the V-blender, degassed, molded, dried, fired, and machined, as in Example 1.

EXAMPLE 6

An acceptable 17 cm×17 cm×7.5 cm billet of material with graded properties, having a density of 0.32 g/cc, and opacified with silicon carbide, was produced using 825 grams of silica fibers, 175 grams of aluminaborosilicate fibers (average diameter-11 microns, 0.64 cm long), 35 grams of 1200 grit silicon carbide, 10 ml of hydrochloric acid, 5 ml of ammonium hydroxide, and deionized water.

The silica fibers were washed in accordance with the procedure of Example 2. The aluminaborosilicate fibers were dispersed in a 7,570 ml V-blender with 5000 grams of deionized water for 5 minutes. The washed silica fibers, dispersed aluminaborosilicate fibers, silicon carbide and ammonium hydroxide were mixed with enough deionized water to bring the total weight to 25,000 grams, in a 28.31 liter V-blender for 15 minutes with the intensifier bar running. The slurry was removed from the V-blender, degassed, molded, dried, fired and machined in accordance with the procedure of Example 1.

The resulting billet of material is relatively richer in silica at the top and aluminaborosilicate at the bottom.

EXAMPLE 7

A 17.5 cm×17.5 cm×9 cm material with a temperature capability greater than that of the material of Example 1, having a density of 0.24 g/cc, and opacified with silicon carbide, was produced using 750 grams of aluminaborosilicate fibers (diameter-1 to 3 microns), 250 grams of silica fibers, 35 grams of silicon carbide, 5 ml of ammonium hydroxide, and deionized water. The silica fibers were dispersed in a 7,570 ml V-blender with 5,000 grams of deionized water for 5 minutes.

The dispersed silica fibers, aluminaborosilicate fibers, silicon carbide, and ammonium hydroxide were mixed with enough deionized water to bring the total weight to 18,000 grams, in a 28.31 liter V-blender for 7 minutes with the intensifier bar running. The slurry was removed from the V-blender, degassed, molded, and dried as in Example 2. In the furnace, the temperature was increased at a rate of 220° C. per hour to the firing temperature of 1370° C. where it was held for 1½ hours. After firing, the temperature was decreased at a rate of 220° C. per hour to 980° C., at which point the furnace was turned off and allowed to cool to room temperature. The billet was machined to 17.5 cm×17.5 cm×9 cm in accordance with the usual machining practices.

The preferred alumina fibers are 95.2% pure and are available from ICI Americas, Inc. and marketed as SAF- FRIL™. The preferred diameter for the alumina fibers ranges from 1 to about 15 microns. The preferred silica fibers are 99.7% pure and are available from Schuller (Johns Manville Corp.), Denver, Colo. and marketed as MICROQUARTZ 108™ fibers or as Q-FIBER™. These fibers have an average diameter of 1.7 microns. However, silica fibers having diameters ranging from 1 to 6 microns are useful in the present invention.

Also, mixtures of the above-described fibers can be used with other fibers known in the art, e.g., zirconium fibers. In addition, metal fibers and carbon fibers can be utilized by themselves or in combination with other fibers. As stated, the product of the method of the present invention to make the filler/reinforcer of the present invention may comprise as much or greater than 99% silica.

While boron nitride is considered to be the preferred boron source, it is believed that $SiBx$, $B_4C$, $B_2O_3$, and B and other boron sources can also be used. It is preferred that boron be present in an amount from about 0.4% to about 3% by weight. Boron nitride is believed to be preferred because it is believed, due to its stability, that it permits a more uniform fusion to fiber junction and yields superior bonding and uniform porosity.

In addition, aluminaborosilicate fibers may be used and are available from 3M Company marketed under the tradename AB-312™ which contains 62% (plus/minus 2.0%) $Al_2O_3$, 14% (plus/minus 2.0%) $B_2O_3$ and 24% (plus/minus 2.0%) $SiO_2$. These fibers are available and useful in the present invention in diameters ranging from 3 to 12 microns.

The preferred composition comprised of: 21% by weight alumina fiber; 74% by weight silica fiber; 2% by weight (600 grit) silicon carbide; and 2.85% by weight boron nitride is also available commercially in densities 3 to 64 lbs./ft.$^3$ (plus/minus ¾ lb.) from Lockheed Missiles and Space Company, Inc., Sunnyvale Calif. ("Lockheed") under the trade name "HTP" (High Temperature Performance). For example, Lockheed commercially sells "HTP-12-22" (12 lb./ft.$^3$ density silica/alumina fiber ratio of 78/22), "HTP-12-35" (12 lb./ft.$^3$ density in a silica/alumina fiber ratio of 65/35) and "HTP-12-45" (12 lb./ft.$^3$ density in silica/alumina fiber ratio of 55/45.

Materials Evolution & Development USA, Inc. manufactures the above types of Ultra-low density fused-fibrous ceramics under the trade name P.R.I.M.M.™ (Polymeric Rigid Inorganic Matrix Material). Materials Evolution & Development USA, Inc. manufacturers P.R.I.M.M.™ in densities varying from 4 lb./ft.$^3$ to 64 lb./ft.$^3$. P.R.I.M.M.™ material is ground by mortar and pestle, or other grinding mechanism, then sieved into different particulate sizes. An optimum sieved particulate size for P.R.I.M.M.™ material (16 lb/ft$^3$ density) is approximately 180 microns in diameter. However, optimum particle sizes are believed to be dependent upon the surface tension and viscosity of the binder used in a particular application and P.R.I.M.M.™ material density and can range from about 150 microns to about 350 microns. The preferred particle size, i.e., the filler or reinforcement particles, of the PRIMM™ product of the present invention ranges from about 180 microns to about 250 microns. In addition, in some applications it is preferable to utilize particles of a smaller size in combination with the above particle size range. For example, in composite resin systems, it is preferable to utilize 3 parts particulates in the 180–250 micron range to 1 part particulates in the 90–125 micron range.

In addition to the filler/reinforcer of the present invention, other fillers known in the art may be utilized in combination in binder systems, for example, microfil fillers selected from the group consisting of inorganic materials, metallic materials, organic materials, and mixtures thereof. Examples include barium glass, zirconium, crystalline carbon and mixtures thereof. Indeed, utilizing the present inventive filler/reinforcer with microfils, a composite resin may comprise over 80% filler loading, preferably over 90% filler loading by weight.

The present invention includes the use of radiopacifiers including, but not limited to, TPB, bismuth, aluminum compounds, metal oxides, and organo-metallic compounds.

The present invention may be utilized with a variety of binder or resin systems including, but not limited to, self-activating, light curable, heat curable, self-curing and microwave curing systems.

The density of the PRIMM™ product, i.e., the filler or reinforcer, of the present invention ranges from about 6 lb/ft$^3$ to about 50 lb/ft$^3$, preferably from about 6 lb/ft$^3$ to about 25 lb/ft$^3$, and most preferably from about 6 lb/ft$^3$ to about 16 lb/ft$^3$.

Figure 3:
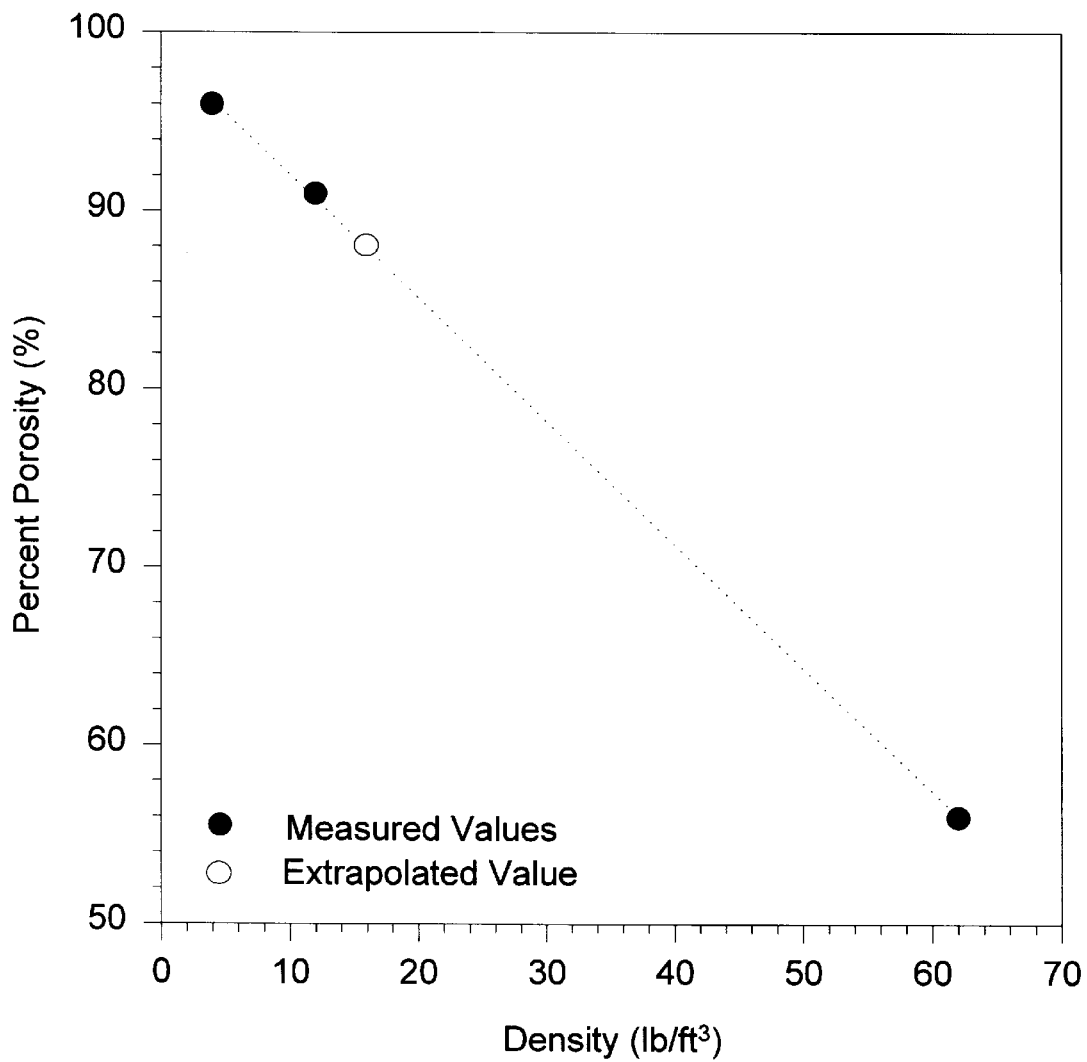
FIG. 3 porosity of function of density.
Figure 4:
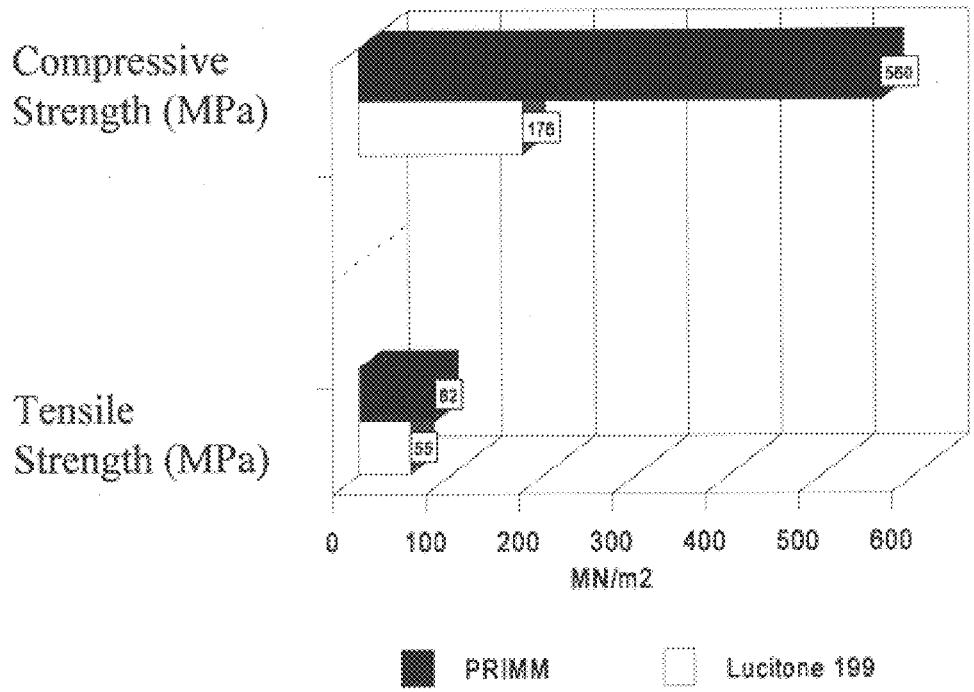
FIGS. 4–7 compressive strength and tensile strength.
Figure 5:
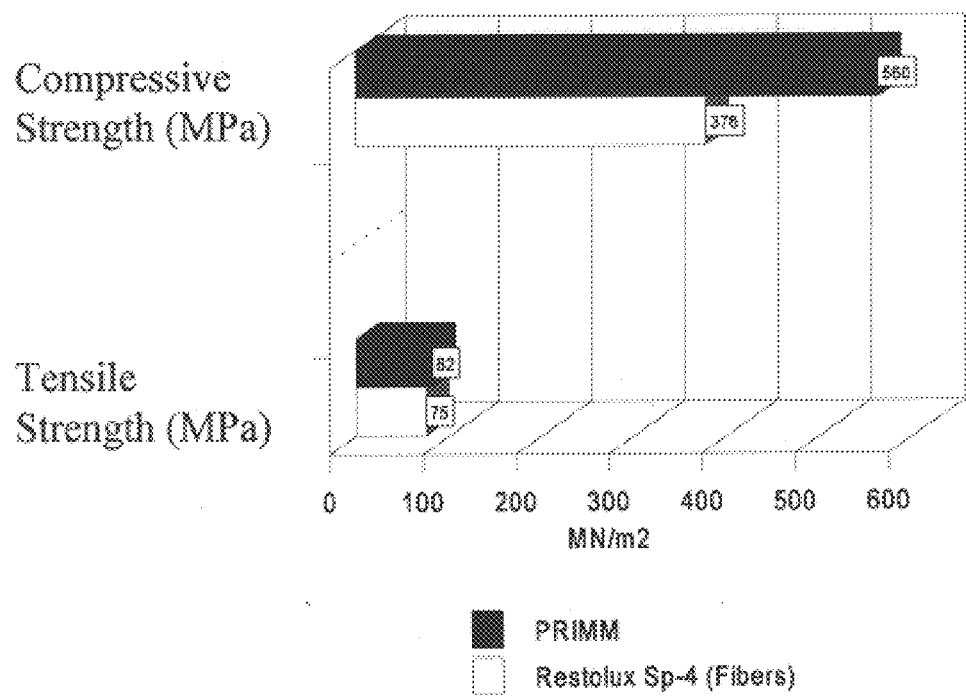
Figure 6:
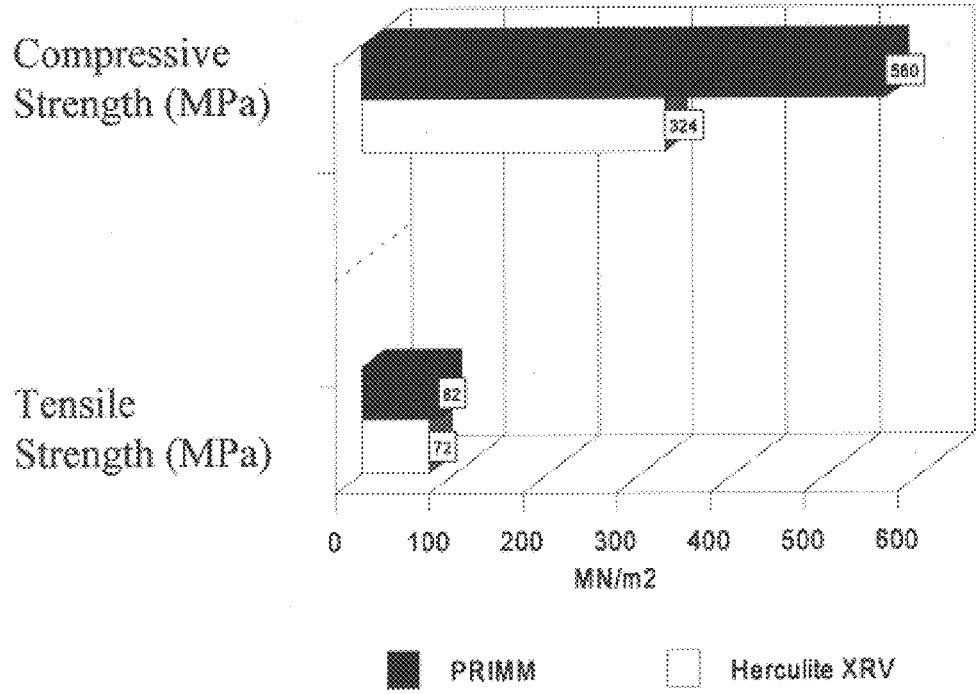
Figure 7:
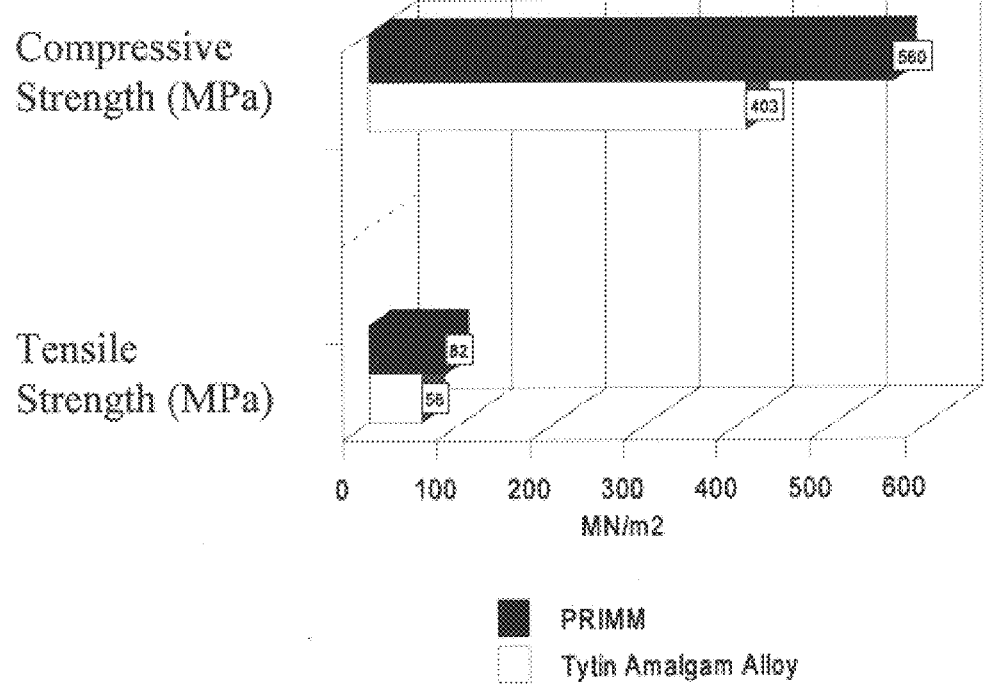

The porosity of the PRIMM™ product, i.e., the filler or reinforcement, of the present invention ranges from about 60% by volume void space and up, preferably the product porosity ranges from about 70% by volume void space and up, and most preferably, the porosity of the reinforcement of the present invention ranges from about 80% by volume void space. For example, 16 lb/ft$^3$ PRIMM™ product of the present invention manufactured utilizing the examples of the present invention comprises approximately 88% by volume void space. The relationship between density and porosity is charted in FIG. 3.

The reinforcement or filler of the present invention (PRIMM™ product) preferably has average or mean pore diameters of greater than 10 microns, more preferably over 20 microns. For example, see FIG. 1, an SEM of an example of the PRIMM™ product of 16 lb/ft$^3$ density, silanated as described herein, and with colloidal silica. As can be seen, the material comprises mean pore diameters greater than 10 microns.

The compressive strength (MN/m$^2$) and tensile strength (MN/m$^2$) of an embodiment of the restorative material of the present invention (78% alumina, 22% silica, % 3 silicon carbide, 2.85% boron nitride at 16 lb/ft$^3$ density) is compared in Tables 1–4 below to commercially available dental restorative materials: "LACITONE 199 DENTURE ACRYLIC" available from Dentsply International, Inc.; "RESTOLUX SP-4 COMPOSITE RESIN" (Chopped Fibers) available from Lee Pharmaceuticals; "HERCULITE XRV" (Kerr) composite resin available from Kerr Manufacturing Co.; "TYTIN AMALGAM ALLOY" available from Kerr Manufacturing Co.

The tensile and compressive strength values of the commercially available materials used for comparison were taken from product information sheets provided by the manufacturers. The method used to determine the tensile strength of the material of the present invention was the Brazilian Test as described in the literature of Craig. (See, Craig, R. G. (1989); *Restorative Dental Materials,* 8 Ed., St. Louis: Mosby, 65-12; 255-92 which is hereby incorporated by reference.) See FIGS. 4–7.

Tables 1–4 illustrate the compressive and tensile strength advantage of the material of the present invention over several commercially available materials. As shown and tested, the material of the present invention has a compressive strength equal to or greater than about 550 MN/m$^2$ and a tensile strength equal to or greater than about 80 MN/m$^2$.

In relation to mixing the filler component of the present invention with a binder to form the composite of the present invention, approximately 1.0 gram of P.R.I.M.M.™ fused-fibrous ceramic product, having a density of 16 lb/ft$^3$ to 28 lb/ft$^3$, was added to approximately 1 gram of GTE resin available from Dentsply and mixed until a complete wetting occurred. It should be noted, that this resin ratio was found to be ideal for easy incorporation and loading beyond this point was detrimental to the ultimate handling of the material. In fact, at a point past this ratio, the composite became very thick and dry and the overloading resulted in unusable material. It is also believed that an increased particle cluster size improves the capillary action of the fibers aligned for an easier incorporation of the resin into the fibers.

It has also been found to be preferable, that once the fibers have been thoroughly mixed into the resin, a known amount of colloidal silica (0.3 grams) ("CABOT-CABOSIL LM 130" fumed silica) was incorporated until the material had a consistency similar to that of currently marketed composite resins. However, unlike currently available composite resins, this mixture proved to be packable and handled much the same way as an amalgam alloy.

It is also believed that the addition of a silanation agent improves the fiber to resin bond. For example, an organofunctional silanation agent (Union Carbide-Silane A-174) was added to the composite. Specifically, 0.1 gram of the silane was added to 1.0 gram of resin prior to mixing it with the fibers. The result of this action produced an intact fiber resin interface bond following the fracturing of the sample. The preferred procedure of silanation of fibers is as follows: (1) mix 4 ml silane (Union Carbide A-179) with 4 ml n-propylamine with 192 ml of cyclohexane for 15 minutes; (2) treat filler fibers for 2 hours in the above prepared solution and stir at room temperature; (3) rinse once with cyclohexane; (4) dry in air at room temperature for 1 hour; and (5) dry at 60° C. for 1 hour. Preferably, the fibers are silanated greater than 90% of the surface area of the fibers.

The silanation process to produce a presilanated binder, e.g., polymer, requires the addition of 0.1% by weight [?] A-174 (Union Carbide Silane; gamma methacryloxy propyltrimethoxy silane) to the predetermined amount of binder needed to formulate the optional fiber-binder ratio prior to mixing.

In addition, it has been found to be preferable when adding the filler/reinforcer of the present invention to resin systems, to do so under vacuum pressure. Also, it is deemed preferable to add the filler/reinforcer of the present invention to resin systems at an elevated temperature, i.e., greater than 25° C. to decrease the viscosity of the resin system.

Preferred organic binders for use with the filler or reinforcement of the present invention include, but are not limited to, acrylate resins, for posterior composite resins, dentures, sealants, laboratory resins, temporary crowns, and denture teeth. For plastic restoration, epoxy resins are preferred.

Preferred inorganic binder for use with the filler/reinforcement of the present invention include, but are not limited to, zinc oxide for bases, zinc phosphate and glass ionomers for cements, 4-meta for bonding agents, calcium hydroxide for liners, and lucite for porcelains.

Preferred metallic binders include, but are not limited to, for use with the filler/reinforcers of the present invention: silver/copper/tin/mercury amalgam, gallium, gold, noble metal and titanium.

Figure 8:
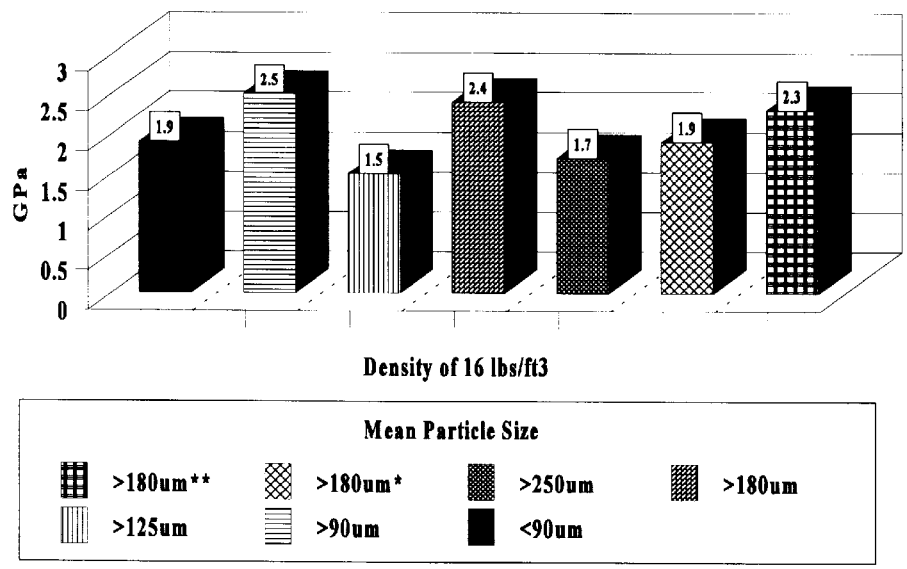
FIG. 8 flexural modulus.

It has also been found that the mean particle size (microns) effects the flexural modulus (Pa×10$^{10}$), compressive strength (MN/m$^2$), and surface roughness (Ra). Shown below in Tables 5–7, is the filler component of the present invention at 16 lb/ft$^3$ density (1:1 filler/resin mixture) for different particle sized (microns). Note, as used below, "Si" means the material includes colloidal silica and "SiTR" means it includes colloidal silica and that the resin was silanated. See FIG. 8.

Figure 9:
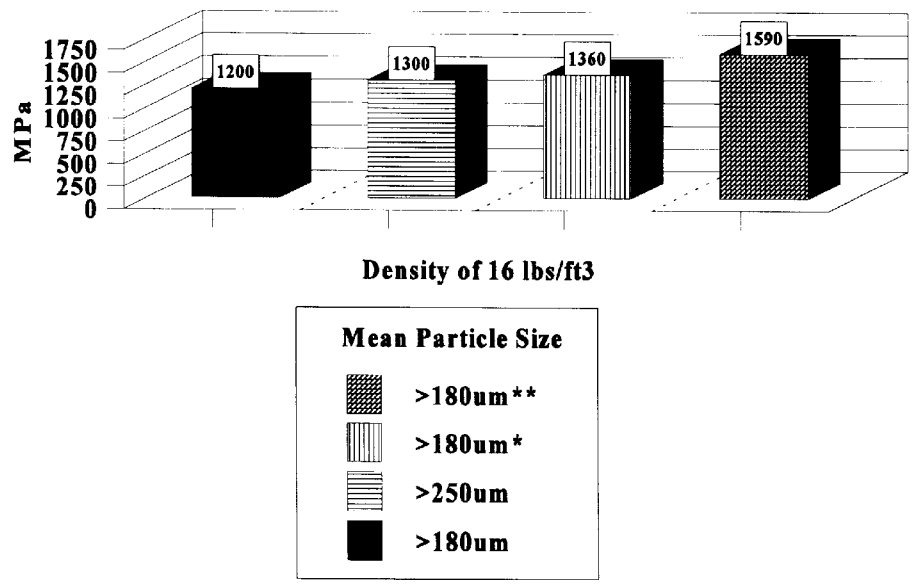
FIG. 9 compressive strength.

FIG. 9. Ideal Modulus form at density 16-Particle size greater than 180 um—with silica (Colloidal) and Silanated Resin.

Figure 10:
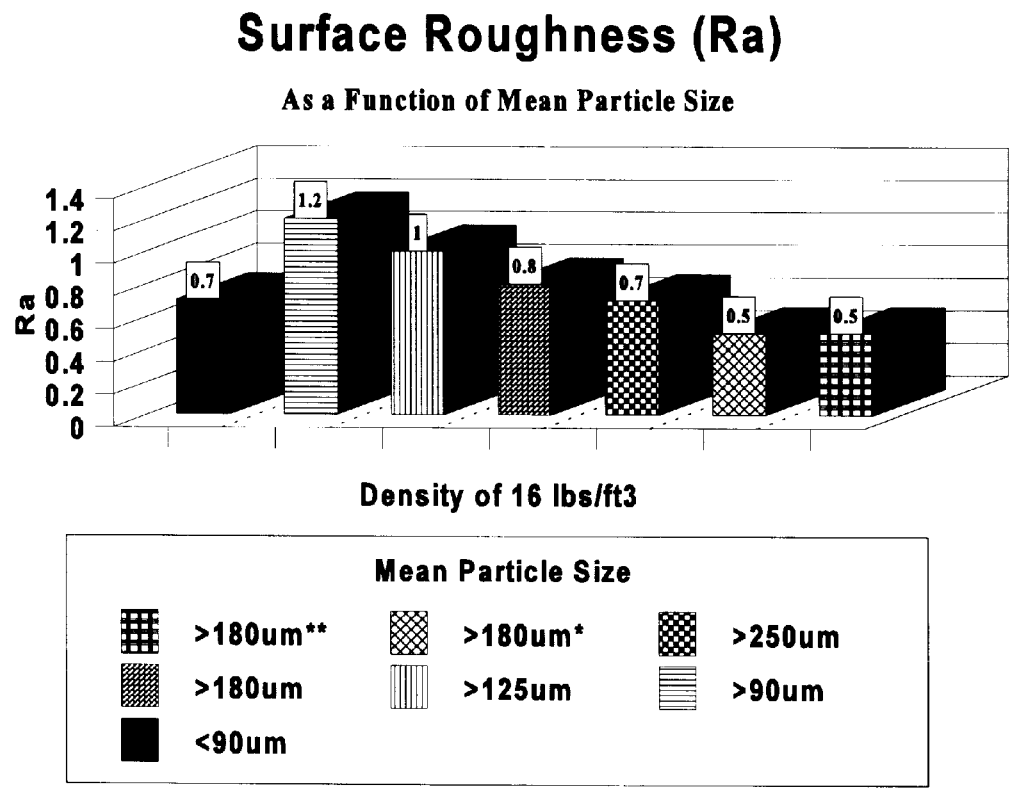
FIG. 10 surface tough.

FIG. 10. Compressive strength exhibited significant improvement with the addition of Colloidal Silica and presilanation of the resin.

TABLE 7. Surface roughness decreased significantly with the addition of silica (Colloidal).

A comparison of the properties of the filler component of the present invention as compared to prior art filler components is shown in Table 8.

TABLE 8

| Product | FCC + Sio$_2$* | Restolux SP-4 ™ | Z100 (3M) | XRV Herco. | TPH Prisma | Heliomolar | Charisma |
|---|---|---|---|---|---|---|---|
| Filler | Alumina/ Silica (Fused Fibers) | Chopped Glass Fibers | Zirconia/ Silica | Barium Glass | Barium Glass | SiO$_3$ | Barium Glass/ Microglass |
| Filler loading Wt (%) | 60 | 68.5 | 66 | 56 | 53 | 38 | 73 |
| Average Particle Size (microns) | 180/0.4 | 300 | 0.6 | 0.6 | 1 | Microfil** (hybrid) | 0.7 |
| Diametral Tensile (MPa) | 82 | ** | 83 | 81 | 72 | 47 | 77 |
| Compressive Strength (MPa) | 560 | 300 | 448 | 324 | 375 | 436 | 399 |
| Hardness (Kg/mm2) | 50 | 125 | 78.3 | 53.3 | 43.5 | 35.9 | ** |
| Y-Modulus (Pa) | 25 × 10$^9$ | 23 × 10$^9$ | 13 × 10$^9$ | 7.6 × 10$^9$ | 5.7 × 109 | 4.3 × 10$^9$ | ++ |
| Surface Roughness (Ra) | 0.30 | 1.19 | 0.27 | 0.12 | 0.29 | .013 | ** |
| Coeff of Thermal Expansion × 10$^6$ unit/unit/C | 10 | 17 | 17 | 27 | 30 | 52 | 38 |

TABLE 8-continued

| Product | FCC + Sio₂* | Restolux SP-4 ™ | Z100 (3M) | XRV Herco. | TPH Prisma | Heliomolar | Charisma |
|---|---|---|---|---|---|---|---|
| Radiopacity | TPB***[Yes] | Yes | Yes | Yes | Yes | Yes | Yes |
| Linear Shrinkage | 6.08 | 0.35 | 0.29 | ** | .03 | ** | ** |

*PRIMM ™ (1.0 g) containing FFC's and colloidal silica of 0.4 mm diameter with 1.0 g Dentsply GTE resin (Bis GMA, Bis EMA, Teg DMA).
**Data unavailable.
****"TPB"-Radiopaque additive of proprietary nature, available from Sluka of Germany having the formula $C_8H_{15}Bi$, equivalent to 16 mm of aluminum.

TABLE 9

PRIMM ™ AUGMENTED AMALGAM

|  | KN | MPa |
|---|---|---|
| Control | 1250 | 99.2 |
| (Dispersalloy ® ) | 1275 | 101.2 |
|  | 1100 | 87.3 |
|  | 1000 | 79.4 |
|  | 1000 | 79.4 |
|  | 1230 | 97.6 |
| 2% PRIMM | 2500 | 198.4 |
|  | 2225 | 176.6 |
|  | 1850 | 146.8 |
|  | 1850 | 146.8 |
|  | 1600 | 127.0 |
|  | 1750 | 138.9 |
| 4% PRIMM | 2050 | 165.9 |
|  | 1750 | 138.9 |
|  | 1850 | 146.8 |
|  | 1800 | 142.9 |
|  | 1650 | 131.0 |
|  | 1600 | 127.0 |

The above results report on incorporation of PRIMM™ (16 lb/ft³) into Dispersalloy® available from Dentsply Caulk. In the above Table, three groups are reported on: (1) 100% Dispersalloy® available from Dentsply Caulk. In the above Table, three groups are reported on: (1) 100% Dispersalloy® (no PRIMM™ product), (2) 98% by weight Dispersalloy® and 2% by weight PRIMM™ product, and (3) 96% by weight Dispersalloy® and 4% by weight PRIMM. The fibers of the PRIMM™ product were presilanated as discussed above. They were then treated with "All-BOND II" available from Bisco, Inc. "All-BOND II" is known as a 4-META adhesive comprising the adhesive molecule 4-methacryloxyethyl trimellitate anhydride. The test specimens were made using 9 mm long polypropylene tubes with an inner diameter of 4 mm. The control specimens were prepared on glass plates and packed into the tubes using standard dentistry procedures. For the augmented specimens, the PRIMM™ product particles were mixed into the amalgam to a uniform consistency and the blend packed into the tubes. After curing, the plastic tubing was removed and the specimens milled to a length of 8 mm. The specimens were tested in an Instron Universal testing machine (available from Instron Corp.). The cylinders were placed in a steel holder which aligned the top surface parallel with the flat surface of the crosshead to insure even distribution of the applied force. The cylinders were subjected to continuous loading at a crosshead speed of 5 mm/min. until fracture. The compressive forces required for fracture were then recorded in Newtons and calculated in Megapascals (Mpm) using the formula:

Fracture force: Newtons

Cylinder surface area: radius=2 mm; area=$\pi(2)^2$=12.6 mm²

Compressive Strength: Fracture force/cylinder surface area=Newtons/mm²=Megapascals.

While the invention has been illustrated and described in detail in the foregoing description, the same is to be considered as illustrative and not restrictive of character, it being understood that only the preferred embodiment has been shown and described and that all changes and modifications that come within the spirit of the invention are desired to be protected.

What is claimed is:

1. In a method for the direct filling of a cavity in a tooth, wherein said method includes filling said cavity with an initially liquid, settable filling material comprising a filler and a binder admixed therewith, thereafter permitting said material to harden in situ, the movements in said method comprising utilizing as the predominant component of said filler, a fused-fibrous material comprised of:

from about 1% to about 50% by weight alumina;

from about 50% to about 98% by weight silica; and from about 1% to about 5% by weight boron.

2. The method of claim 1 wherein the filler is comprised of from about 15% to about 30% by weight alumina and from about 65% to about 85% silica.

3. The method of claim 1 wherein the fused-fibrous material has mean pore diameters of greater than 10 microns.

4. The method of claim 1 wherein the fused-fibrous material is greater than 60% by volume void space.

5. The method of claim 1 wherein the fused-fibrous material is in particle form.

6. The method of claim 5 wherein the particles have diameters of about 150 microns to about 350 microns.

7. The method of claim 6 further comprising particles having diameters less than or equal to 5 microns.

8. A fused-fibrous dental restorative composition comprising:

a binder; and a filler, said filler comprised of about 1% to about 50% by weight alumina, from about 50% to about 98% percent by weight silica, and boron.

9. The composition of claim 8 further comprising silicon carbide.

10. The composition of claim 8 wherein the filler is comprised of about 15% to about 30% by weight alumina and about 65% to about 85% silica.

11. The composition of claim 8 wherein the filler is comprised of about 21% by weight alumina and about 74% by weight silica.

12. A method for the filling of a cavity in a tooth comprising:

(a) filling said cavity with a settable filling material comprising a binder and filler, wherein said filler com prises at least 60% by volume void space and has mean pore diameters of greater than 10 microns and (b) thereafter allowing said material to harden.

13. The method of claim 12 wherein the filler is comprised of alumina and silica.

14. The method of claim 13 wherein the filler further comprises boron.

15. A fused-fibrous ceramic dental restorative composition manufactured from:

alumina fibers, silica fibers and from about 1% to about 5% boron nitride.

16. The composition of claim 15 further manufactured from silicon carbide.

17. The composition of claim 15 manufactured from about 2.85% by weight boron nitride.

18. The composition of claim 15 manufactured from about 21% by weight alumina.

19. The composition of claim 15 manufactured from about 74% by weight silica.

20. The composition of claim 15 manufactured from alumina fibers having an average diameter of from about 1 to about 15 microns.

21. The composition of claim 15 manufactured from silica fibers having an average diameter of from about 1 to about 6 microns.

22. A fused-fibrous dental restorative composition comprising:

alumina; and silica; whereby said composition is greater than about 60% by volume void space and has mean pore diameters greater than about 10 microns.

23. The composition of claim 22 comprising from about 1% to about 50% by weight alumina.

24. The composition of claim 22 comprising from about 50% to about 98% by weight silica.

25. A porous reinforcement for dental restoration materials comprising:

a rigid three-dimensional network of fibers fused together at their points of contact wherein said network has mean pore diameters greater than 10 microns.

26. The reinforcement of claim 25 wherein the network is greater than 60% by volume void space.

27. The reinforcement of claim 25 wherein the fibers are inorganic.

28. The reinforcement of claim 25 wherein the fibers are organic.

29. The reinforcement of claim 25 wherein the fibers are silanated.

30. A porous reinforcement for dental restoration materials comprising:

a rigid three-dimensional network of fibers fused together at their points of contact wherein said network is greater than 60% by volume void space.

31. The reinforcement of claim 30 wherein the fibers are inorganic.

32. The reinforcement of claim 30 wherein the fibers are organic.

33. The reinforcement of claim 30 wherein the reinforcement has mean pore diameters greater than about 10 microns.

34. The reinforcement of claim 30 wherein the fibers are silanated.

* * * * *